United States Patent [19]

Chibata et al.

[11] 4,401,820
[45] Aug. 30, 1983

[54] PROCESS FOR RACEMIZING OPTICALLY ACTIVE α-AMINO ACIDS OR A SALT THEREOF

[75] Inventors: Ichiro Chibata, Suita; Shigeki Yamada, Toyonaka; Chikara Hongo, Osaka; Ryuzo Yoshioka, Kaizuka, all of Japan

[73] Assignee: Tanabe Seiyaku Co., Ltd., Osaka, Japan

[21] Appl. No.: 337,322

[22] Filed: Jan. 5, 1982

[30] Foreign Application Priority Data

Jan. 23, 1981 [JP] Japan .................................. 56-9380
Jun. 19, 1981 [JP] Japan ................................ 56-95765

[51] Int. Cl.$^3$ ................ C07D 233/64; C07D 207/12; C07D 209/20; C07B 20/00

[52] U.S. Cl. ................................. 548/344; 548/496; 548/572; 562/401

[58] Field of Search ............. 260/326.4, 326.43, 326.8, 260/326.14 T; 548/344, 496, 572; 562/401

[56] References Cited

U.S. PATENT DOCUMENTS 2,071,327  2/1937  Bley ............................. 562/401
3,458,568  7/1969  Ogasawara et al. ............ 562/401

Primary Examiner—Natalie Trousof
Assistant Examiner—Vera C. Clarke
Attorney, Agent, or Firm—Jordan B. Bierman; Linda Bierman

[57] ABSTRACT

DL-α-amino acids or a salt thereof can be obtained by racemizing an optically active α-amino acid or a salt thereof in the presence of an aliphatic acid and an aldehyde.

11 Claims, No Drawings

PROCESS FOR RACEMIZING OPTICALLY ACTIVE α-AMINO ACIDS OR A SALT THEREOF

This invention relates to a process for racemizing optically active α-amino acids or a salt thereof.

Synthetic α-amino acid is a mixture of two enantiomers, i.e., D- and L-enantiomers, and such racemate may be resolved into each enantiomers by chemical or biological methods. However, since in almost all of α-amino acids only one enantiomer of the racemate has an economical use, it is desirable to racemize the unwanted enantiomer obtained by optical resolution in order to make it available again for the resolution process.

Various methods have been known for racemization of optically active free α-amino acids. For example, an optically active α-amino acid can be racemized (i) by heating it in water in the presence of either a strong base or a strong acid [Advances in Protein Chemistry, Vol. 4, 339 (1948)]; (ii) by heating it in water without using a strong base and a strong acid [U.S. Pat. No. 3,213,106]; or (iii) by heating it in water in the presence of an aldehyde and a metal ion under neutral or alkaline conditions [Japanese Patent Publication (examined) Nos. 21517/1961 and 13445/1967]. Said racemization of an optically active α-amino acid may also be conducted (iv) by heating it in water under alkaline conditions in the presence of cupric ion and a resinous catalyst which is prepared from a resin such as salicylic acid-phenol-formaline resin [Bulletin of the Chemical Society of Japan, Vol. 36, 734 (1963)]; or (v) by heating it in a lower aliphatic acid [Journal of the Chemical Society of Japan, Vol. 80, 1035(1959)].

Moreover, methods have been known for racemization of the salts of lysine and phenylglycine. For example, optically active lysine p-aminobenzenesulfonate is racemized by heating it in water [British Pat. No. 1,191,100]. On the other hand, optically active phenylglycine benzenesulfonate is racemized by heating it in an aqueous benzenesulfonic acid solution [Japanese patent publication (unexamined) No. 67246/1973].

However, the known methods mentioned above are still unsatisfactory. For example, because of the low velocity of racemization, the racemization reaction of the methods (i) and (ii) must be carried out at a temperature higher than 160° C. in a sealed reactor in order to increase the degree of racemization. These methods (i) and (ii) also result in decomposition of the α-amino acid. In the method (iii) it is a must to use a metal ion for formation of a chelate compound with Schiff base of the α-amino acid, and the excess of the metal ion used therein must be neutralized with an acid prior to recovery of the DL-α-amino acid. In this method, therefore, complicated procedures are inevitably required to avoid contamination with minerals produced during said neutralization step. The method (iv) requires complicated procedures for synthesis of the resinous catalyst. According to the method (v), it is difficult to accomplish the complete racemization of glutamic acid, histidine, isoleucine, cystine, proline and tyrosine. Moreover, in the methods described in British Pat. No. 1,191,100 and Japanese patent publication (unexamined) No. 67246/1974 it is difficult to carry out the racemization reaction without decomposition of the α-amino acid and resolving agents because said racemization must be carried out at such a high temperature as 140° to 190° C.

An object of the present invention is to provide a novel and economical method for racemization of optically active α-amino acids. Another object of the invention is to provide a method of producing DL-α-amino acids or salts thereof in high yield from the corresponding optically active α-amino acids or salts thereof. Another object is to provide a method which makes it possible to carry out the racemization of optically active α-amino acids or salts thereof under mild conditions such as at a temperature of 60° to 100° C. without substantial decomposition of the α-amino acids.

According to the method of the present invention, DL-α-amino acids or a salt thereof can be obtained by racemizing an optically active α-amino acid or a salt thereof in the presence of an aliphatic acid and an aldehyde.

A wide variety of optically active α-amino acids or salts thereof can be racemized according to the method of the present invention. Examples of the α-amino acids to be used in the present invention include a neutral α-amino acid such as alanine, valine, leucine, isoleucine, serine, threonine, cystine, cysteine, methionine, tryptophan, phenylalanine, tyrosine, dopa (i.e., 3-(3,4-dihydroxyphenyl)alanine), phenylglycine or p-hydroxyphenylglycine; a basic α-amino acid such as arginine, lysine, ornithine or histidine; an acidic α-amino acid such as aspartic acid or glutamic acid; and an α-imino acid such as proline or hydroxyproline. The α-amino acids mentioned above can be employed in the form of either free acid or salt thereof for the racemization reaction of the present invention. Examples of the salt of the α-amino acid include the salt of the α-amino acid with an inorganic acid such as hydrochloric acid, sulfuric acid or hydrobromic acid; the salt of the α-amino acid with an organic acid such as oxalic acid, tartaric acid, benzenesulfonic acid, toluenesulfonic acid, xylenesulfonic acid, chlorobenzenesulfonic acid, nitrobenzenesulfonic acid, naphthalenesulfonic acid or methanesulfonic acid; and the salt of the α-amino acid with an alkali metal such as sodium or potassium. Among them, suitable salts are the salt of the neutral or basic α-amino acid with the inorganic or organic acid and the salt of the acidic α-amino acid with the alkali metal. The optically active α-amino acid or a salt thereof to be employed in the present invention may be either optically pure or optically impure.

The racemization reaction of the present invention can be accomplished by contacting an optically active α-amino acid or a salt thereof with an aliphatic acid and an aldehyde. Suitable examples of the aliphatic acid is a compound of the formula:

$$R^1\text{—COOH} \qquad (I)$$

wherein $R^1$ is hydrogen or alkyl of one to 4 carbon atoms. Representative examples of such aliphatic acid include formic acid, acetic acid, propionic acid, butyric acid and valeric acid. Among them, a preferred subgenus is the compound of the formula (I) in which $R^1$ is hydrogen or alkyl of one to 3 carbon atoms. More preferred subgenus is acetic acid and propionic acid. It is preferred to use 2 to 50 g of the aliphatic acid per g of the optically active α-amino acid or a salt thereof. When the aliphatic acid is used in the form of an aqueous solution thereof, the preferred concentration of said aliphatic acid in the solution is 10 to 100 v/v %, especially 60 to 100 v/v %.

On the other hand, suitable example of the aldehyde is a compound of the formula:

$$R^2\text{—CHO} \qquad (II)$$

wherein $R^2$ is hydrogen; alkyl of one to 6 carbon atoms; alkenyl of 2 to 4 carbon atoms; phenyl; phenyl having at least one substituent selected from the class consisting of hydroxy, nitro, amino and alkoxy of one to 4 carbon atoms; phenylvinyl; oxygen-containing heteromonocyclic group; or hydroxynaphthyl. Examples of such aldehyde include those of the formula (I) in which $R^2$ is hydrogen; alkyl of one to 6 carbon atoms such as methyl, ethyl, propyl, isopropyl, butyl, isobutyl, pentyl or hexyl; alkenyl of 2 to 4 carbon atoms such as vinyl, propenyl or butenyl; phenyl; phenyl having at least one substituent selected from the class consisiting of hydroxy, nitro, amino and alkoxy of one to 4 carbon atoms such as methoxy, ethoxy, propoxy or butoxy; phenylvinyl; oxygen-containing heteromonocyclic group such as furyl or nitrofuryl; and hydroxynaphthyl. Representative examples of such aldehyde include formaldehyde, acetoaldehyde, propionaldehyde, n-butyraldehyde, isobutyraldehyde, n-valeraldehyde, caproaldehyde, n-heptylaldehyde, acrylaldehyde (i.e., acrolein), methacrylaldehyde (i.e., methacrolein), salicylaldehyde, m-hydroxybenzaldehyde, p-hydroxybenzaldehyde, o-nitrobenzaldehyde, m-nitrobenzaldehyde, 5-nitrosalicylaldehyde, anisaldehyde, o-aminobenzaldehyde, vaniline, naphtholaldehyde, phenylacrolein, furfural and nitrofurfural. Among them, a preferred subgenus is the compound of the formula (I) in which $R^2$ is hydrogen; alkyl of one to 6 carbon atoms; vinyl; phenyl; phenyl having at least one substituent selected from the class consisting of hydroxy, nitro and methoxy; and furyl. Another preferred subgenus is formaldehyde, acetoaldehyde, propionaldehyde, n-butyraldehyde, n-heptylaldehyde, acrolein, benzaldehyde, salicylaldehyde, p-hydroxybenzaldehyde, p-anisaldehyde, o-nitrobenzaldehyde, 5-nitrobenzaldehyde or furfural. Further preferred subgenus is propionaldehyde, n-butyraldehyde, benzaldehyde and salicylaldehyde. It is preferred to use 0.001 to 0.5 mole, especially 0.005 to 0.2 mole, more especially 0.01 to 0.2 mole, of the aldehyde per mole of the optically active α-amino acid or a salt thereof.

The racemization reaction of the present invention is preferably carried out by mixing the optically active α-amino acid or a salt thereof with the aliphatic acid and the aldehyde, and then stirring the mixture at a temperature of 20° to 120° C., especially 40° to 100° C., more especially 60° to 100° C. In carrying out the racemization reaction, it is not critical to use a solvent because in many cases the aliphatic acid used can well dissolve the optically active α-amino acid or a salt thereof. If required, however, a solvent which is inert to and dissolves the α-amino acid or a salt thereof, the aliphatic acid and the aldehyde may be employed in the present invention. Examples of such solvent include water, benzene and toluene. When the α-amino acid or a salt thereof has insufficient solubility in the aliphatic acid, it is preferred to carry out the racemization in the solvent.

When the optically active α-amino acid in the form of a salt thereof is used in the method of the present invention, the racemization of said α-amino acid salt can be facilitated by carrying it out in the presence of a free DL-α-amino acid. Any kinds of free DL-α-amino acid may be used for this purpose irrespective of the optically active α-amino acid salt used. From a practical viewpoint, however, it is generally preferred to use the free DL-α-amino acid corresponding to the optically active α-amino acid salt which is used for the racemization. It is also preferred to use 0.001 to 0.8 mole of the free DL-α-amino acid per mole of the optically active α-amino acid salt used.

After the reaction, the DL-α-amino acid or a salt thereof can be recovered by a conventional method, for example, by cooling the reaction mixture to crystallize out the DL-α-amino acid or a salt thereof. Alternatively, the recovery of the DL-α-amino acid or a salt thereof can be carried out by condensing the reaction mixture under reduced pressure and then adding alkanol (e.g., methanol, ethanol) or acetone to the residue to precipitate the crystals of DL-α-amino acid or a salt thereof. In the case where the optically active α-amino acid salt is racemized in the presence of the free DL-amino acid, it is preferred that the free DL-α-amino acid used is converted into the same salt as the racemized α-amino acid salt by adding to the reaction mixture one mole of an acid or alkali metal per mole of the free DL-α-amino acid.

The method of the present invention is advantageous in that DL-α-amino acids or a salt thereof can be readily obtained in a high yield. Further, the method of the invention is advantageous in that the racemization reaction can be carried out under mild conditions without decomposing the α-amino acid. Furthermore, the method of the invention is advantageous in that it can apply to a wide variety of α-amino acids or a salt thereof.

Concomitantly, the aldehyde used in the methods described in Japanese patent publication (examined) Nos. 21517/1961 and 13445/1967 is reacted with an α-amino acid to give a shiff base which forms a chelate compound with a metal ion. In this case, therefore, the reaction of the aldehyde with the α-amino acid is carried out under neutral or alkaline conditions. On the other hand, the racemization reaction of the present invention is carried out in the presence of an aliphatic acid (i.e., under acidic conditions) without using a metal ion. Accordingly, the aldehyde used in the present invention is quite different in its mechanism of action from the aldehyde used in the known methods.

EXPERIMENT 1

0.1 g of each one of L-amino acids shown in Table 1 was dissolved in 3 ml of glacial acetic acid, and 0.2 mole of salicylaldehyde per mole of said L-amino acid was added thereto. The mixture was heated at 100° C. for one hour in a sealed tube. After the reaction, 10 ml of 1 N hydrochloric acid were added to the reaction mixture. Then, the optical rotation of the mixture was examined, and the degree of racemization was calculated therefrom.

The results are shown in Table 1. For comparison, the results of the racemization reactions which were carried out without using salicylaldehyde are also shown in Table 1.

It is clear from Table 1 that, when the racemization reaction was carried out in the presence of both glacial acetic acid and salicylaldehyde, every L-amino acids could be racemized almost completely. Further, in this case no decomposition of the amino acid occurred during the reaction.

Concomitantly, no substantial racemization of L-amino acids used were observed when the reaction was carried out in water in the absence of glacial acetic acid or both glacial acetic acid and salicylaldehyde.

TABLE 1

| Amino acid (L-form) | Acetic acid*1 | Salicyl-aldehyde*1 | Racemization (%) |
|---|---|---|---|
| Alanine | (+) | (+) | 100 |
|  |  | (−) | 9 |
| Arginine | (+) | (+) | 100 |
|  |  | (−) | 9 |
| Glutamic acid*2 | (+) | (+) | 81 |
|  |  | (−) | 51 |
| Isoleucine*3 | (+) | (+) | 93 |
|  |  | (−) | 4 |
| Leucine | (+) | (+) | 100 |
|  |  | (−) | 23 |
| Lysine | (+) | (+) | 100 |
|  |  | (−) | 9 |
| Methionine | (+) | (+) | 100 |
|  |  | (−) | 24 |
| Phenylalanine | (+) | (+) | 100 |
|  |  | (−) | 35 |
| Proline*4 | (+) | (+) | 91 |
|  |  | (−) | 3 |
| Serine*5 | (+) | (+) | 81 |
|  |  | (−) | 0 |
| Valine | (+) | (+) | 89 |
|  |  | (−) | 4 |

Note:
*1 (+) means that the racemization reaction was carried out in the presence of acetic acid or salicylaldehyde, and (−) means that the reaction was carried out in the absence of acetic acid or salicylaldehyde.
*2 The racemization reaction was carried out at 100° C. for 2 hours by using 80% acetic acid.
*3 The epimerization occurred, and a mixture of L-isoleucine and D-alloisoleucine was obtained from L-isoleucine.
*4 The racemization reaction was carried out by using 0.6 ml of glacial acetic acid.
*5 The racemization reaction was carried out at 80° C. by using 95% acetic acid.

EXPERIMENT 2

3 ml of an aliphatic acid shown in Table 2, 0.1 g of an L-amino acid shown in Table 2 and 0.2 mole of salicylaldehyde per mole of said L-amino acid were admixed, and the mixture was stirred at 100° C. for one hour. After the reaction, the degree of racemization of L-amino acid was estimated in the same manner as described in Experiment 1.

The results are shown in Table 2. For comparison, the results of the racemization reactions which were carried out without using salicylaldehyde are also shown in Table 2.

It is clear from Table 2 that, when the racemization reactions of L-amino acids were carried out in the presence of both the aliphatic acid and salicylaldehyde, DL-amino acids could be obtained in a high yield.

TABLE 2

| L-amino acid | Aliphatic acid | Racemization (%) Salicylaldehyde* | |
|---|---|---|---|
|  |  | (−) | (+) |
| L-Alanine | 97% formic acid | 53 | 81 |
| L-Lysine | 97% formic acid | 19 | 43 |
| L-Lysine | 99.7% propionic acid | 19 | 96 |
| L-Methionine | 97% formic acid | 18 | 49 |
| L-methionine | 99.7% propionic acid | 19 | 96 |

Note:
*(+) means that the racemization reaction was carried out in the presence of salicylaldehyde, and ( ) means that the reaction was carried out in the absence of salicylaldehyde.

EXPERIMENT 3

0.1 g of an L-amino acid shown in Table 3 was dissolved in 3 ml of glacial acetic acid, and 0.2 mole of an aldehyde shown in Table 3 per mole of said L-amino acid was added thereto. The mixture was heated at 80° C. or 100° C. for one hour. After the reaction, the degree of racemization of L-amino acid was estimated in the same manner as described in Experiment 1.

The results are shown in Table 3. For comparison, the results of the racemization reactions which were carried out without using the aldehyde are also shown in Table 3.

It is clear from Table 3 that the racemization of L-amino acids was facilitated by carrying it out in the presence of the aliphatic or aromatic aldehyde.

TABLE 3

| Aldehyde | Temperature | Racemization (%) L-Amino acids* | | | |
|---|---|---|---|---|---|
|  |  | I | II | III | IV |
| — | 80° C. | 7 | 0 | 35 | 0 |
|  | 100° C. | 13 | 24 | 35 | 3 |
| Formaldehyde | 100° C. | 83 | 95 | 100 | 63 |
| Acetaldehyde | 100° C. | 97 | 100 | 100 | 98 |
| Propionaldehyde | 80° C. | 78 | 100 | 100 | 87 |
| n-Butyraldehyde | 80° C. | 97 | 95 | 100 | 99 |
| n-Heptylaldehyde | 100° C. | 100 | 100 | 100 | 100 |
| Acrolein | 100° C. | 76 | 100 | 100 | 100 |
| Benzaldehyde | 80° C. | 72 | 100 | 100 | 72 |
| Salicylaldehyde | 100° C. | 100 | 100 | 100 | 91 |
| p-Hydroxybenzaldehyde | 80° C. | 75 | 100 | 100 | 48 |
| p-Anisaldehyde | 80° C. | 80 | 100 | 100 | 56 |
| o-Nitrobenzaldehyde | 80° C. | 100 | 100 | 100 | 34 |
| 5-Nitrosalicylaldehyde | 80° C. | 100 | 100 | 100 | 91 |
| Furfural | 100° C. | 100 | 100 | 100 | 100 |

Note:
*I: L-Alanine
II: L-Methionine
III: L-Phenylalanine
IV: L-Proline

EXPERIMENT 4

0.1 g of L-alanine was dissolved in 3 ml of glacial acetic acid. To the solution was added salicylaldehyde at a molar ratio shown in Table 4. The mixture was stirred at 100° C. for one hour. After the reaction, the degree of the racemization of L-alanine was estimated in the same manner as described in Experiment 1.

The results are shown in Table 4.

TABLE 4

| Molar ratio of salicylaldehyde to L-alanine | Racemization (%) |
|---|---|
| 0 | 9 |
| 0.001 | 44 |
| 0.005 | 87 |
| 0.01 | 100 |
| 0.05 | 100 |
| 0.1 | 100 |
| 0.2 | 100 |

EXPERIMENT 5

0.1 g of an L-amino acid shown in Table 5, 3 ml of glacial acetic acid and 0.2 mole of salicylaldehyde per mole of said L-amino acid were admixed, and the mixture was stirred at 40° C., 60° C., 80° C. or 100° C. for one hour. After the reaction, the degree of the racemization of L-amino acid was estimated in the same manner as described in Experiment 1.

The results are shown in Table 5. For comparison, the results of the racemization reactions which were carried out without using salicylaldehyde are also shown in Table 5.

TABLE 5

| L-Amino acid | Molar ratio of salicylaldehyde to L-amino acid | Racemization (%) | | | |
|---|---|---|---|---|---|
| | | 40° C. | 60° C. | 80° C. | 100° C. |
| L-Alanine | 0 | 0* | 0* | 7* | 13 |
| | 0.2 | 33* | 55* | 72* | 100 |
| L-Lysine | 0 | 0 | 4 | 5 | 9 |
| | 0.2 | 47 | 100 | 100 | 100 |
| L-Methionine | 0 | 0 | 0 | 0 | 24 |
| | 0.2 | 72 | 97 | 100 | 100 |
| L-Phenylalanine | 0 | 23 | 25 | 30 | 35 |
| | 0.2 | 77 | 86 | 95 | 100 |

Note:
*The racemization reaction was carried out by suspending L-amino acid in glacial acetic acid.

EXPERIMENT 6

0.1 g of L-phenylalanine was dissolved in an aqueous acetic acid solution, and 0.2 mole (0.013 ml) of salicylaldehyde per mole of said L-phenylalanine was added thereto. The mixture was stirred at 100° C. for one or three hours. After the reaction, the degree of the racemization of L-phenylalanine was estimated in the same manner as described in Experiment 1.

The results are shown in Tables 6 and 7. For comparison, the results of the racemization reactions which were carried out without using salicylaldehyde are also shown in Tables 6 and 7.

It is clear from Tables 6 and 7 that, when the racemization reaction was carried out in the presence of salicylaldehyde, the degree of racemization of L-amino acids increased with an increase in the concentration (V/V %) of acetic acid. Moreover, Tables 6 and 7 show that no substantial racemization occurred in an aqueous solution containing less than 50 V/V % of acetic acid if the racemization reaction was carried out in the absence of salicylaldehyde. In contrast thereto, when the racemization reaction was carried out in the presence of salicylaldehyde, the racemization of L-phenylalanine occurred even in an aqueous 10 V/V % acetic acid solution.

TABLE 6

(Reaction time: one hour)

| Concentration of acetic acid (v/v %) | Racemization (%) Salicylaldehyde* | |
|---|---|---|
| | (+) | (−) |
| 10 | 6 | 0 |
| 20 | 14 | 0 |
| 30 | 17 | 0 |
| 40 | 28 | 0 |
| 50 | 32 | 0 |
| 60 | 42 | 2 |
| 70 | 52 | 12 |
| 80 | 71 | 21 |
| 90 | 100 | 25 |

TABLE 6-continued (Reaction time: one hour)

| Concentration of acetic acid (v/v %) | Racemization (%) Salicylaldehyde* | |
|---|---|---|
| | (+) | (−) |
| 100 | 100 | 35 |

TABLE 7

(Reaction time: 3 hours)

| Concentration of acetic acid (v/v %) | Racemization (%) Salicylaldehyde* | |
|---|---|---|
| | (+) | (−) |
| 10 | 18 | 0 |
| 20 | 40 | 0 |
| 30 | 59 | 0 |
| 40 | 70 | 0 |
| 50 | 80 | 2 |
| 60 | 87 | 4 |
| 70 | 95 | 15 |

Note:
*(+) in Tables 6 & 7 means that the racemization reaction was carried out in the presence of salicylaldehyde, and (−) means that the reaction was carried out in the absence of salicylaldehyde.

EXPERIMENT 7

0.1 g of an L-amino acid salt shown in Table 8 was dissolved in 3 ml of glacial acetic acid, and salicylaldehyde was added thereto. The mixture was heated at 100° C. for 3 hours in a sealed tube. After the reaction, the degree of the racemization of L-amino acid salt was estimated in the same manner as described in Experiment 1.

The results are shown in Table 8. For comparison, the results of the racemization reactions which were carried out without using salicylaldehyde are also shown in Table 8.

It is clear from Table 8 that, when the reaction was carried out in the presence of both acetic acid and salicylaldehyde, DL-amino acid salts could be obtained in a high yield. Further, in this case, no decomposition of the amino acid salt occurred during the reaction.

Concomitantly, no substantial racemization of L-amino acid salts were observed when the reaction was carried out in water in the absence of glacial acetic acid or both glacial acetic acid and salicylaldehyde.

TABLE 8

| Amino acid salt (L-form) | Molar ratio of salicylaldehyde to L-amino acid salt*[1] | Racemization (%) |
|---|---|---|
| Alanine hydrochloride | 0.05 | 77 |
| | (−) | 8 |
| Alanine benzenesulfonate | 0.2 | 70 |
| | (−) | 0 |
| Arginine hydrochloride*[2] | 0.05 | 100 |
| | (−) | 25 |
| Leucine benzenesulfonate | 0.2 | 54 |
| | (−) | 0 |
| Lysine hydrochloride*[2] | 0.1 | 100*[4] |
| | (−) | 14*[4] |
| Lysine dl-tartrate*[2] | 0.1 | 100 |
| | (−) | 55 |
| Methionine hydrochloride | 0.1 | 97 |
| | (−) | 7 |
| Phenylalanine hydrochloride | 0.05 | 100 |
| | (−) | 50 |
| Phenylalanine p-xylenesulfonate | 0.2 | 100 |
| | (−) | 46 |
| Glutamic acid | 0.2 | 100 |

TABLE 8-continued

| Amino acid salt (L-form) | Molar ratio of salicylaldehyde to L-amino acid salt[*1] | Racemization (%) |
|---|---|---|
| monosodium salt[*3] | (−) | 0 |

Note:
[*1] (−) means that the racemization reaction was carried out in the absence of salicylaldehyde.
[*2] The salt consists of one mole of the amino acid and one mole of the acid.
[*3] The racemization reaction was carried out by using an aqueous 90% acetic acid instead of glacial acetic acid.
[*4] The racemization reaction was carried out by suspending the L-amino acid salt in the aliphatic acid.

EXPERIMENT 8

0.1 g of an L-amino acid salt shown in Table 9 was dissolved in 3 ml of propionic acid, and 0.2 mole of salicylaldehyde per mole of said L-amino acid salt was added thereto. The mixture was stirred at 100° C. for 3 hours. After the reaction, the degree of the racemization of the L-amino acid salt was estimated in the same manner as described in Experiment 1.

The results are shown in Table 9. For comparison, the results of the racemization reactions which were carried out without using salicylaldehyde are also shown in Table 9.

It is clear from Table 9 that, when the reaction was carried out in the presence of both propionic acid and salicylaldehyde, the DL-amino acid salts could be obtained in a high yield.

TABLE 9

| Amino acid salt (L-form) | Salicylaldehyde[*1] | Racemization (%) |
|---|---|---|
| Alanine benzenesulfonate | (+) | 67 |
|  | (−) | 4 |
| Lysine hydrochloride | (+) | 47[*2] |
|  | (−) | 0[*2] |
| Methionine hydrochloride | (+) | 100 |
|  | (−) | 4 |
| Phenylalanine hydrochloride | (+) | 100 |
|  | (−) | 34[*2] |

Note:
[*1] (+) means that the racemization reaction was carried out in the presence of salicylaldehyde, and (−) means that the reaction was carried out in the absence of salicylaldehyde.
[*2] The racemization reaction was carried out by suspending L-amino acid salt in propionic acid.

EXPERIMENT 9

0.1 g of L-alanine hydrochloride was dissolved in 3 ml of glacial acetic acid, and 0.1 mole of an aldehyde shown in Table 10 per mole of said L-alanine hydrochloride was added thereto. The mixture was stirred at 100° C. for 3 hours. After the reaction, the degree of the racemization of L-alanine hydrochloride was estimated in the same manner as described in Experiment 1.

The results are shown in Table 10. It is clear from Table 10 that the aldehyde, either aliphatic or aromatic, could facilitate the racemization of L-alanine hydrochloride.

TABLE 10

| Aldehyde | Racemization (%) |
|---|---|
| (The method of the present invention) | |
| n-Heptylaldehyde | 47 |
| Benzaldehyde | 52 |
| Salicylaldehyde | 87 |
| o-Nitrobenzaldehyde | 52 |
| Furfural | 95 |

TABLE 10-continued

| Aldehyde | Racemization (%) |
|---|---|
| (Control) | |
| No addition | 6 |

EXPERIMENT 10

0.1 g of an L-amino acid salt shown in Table 11 was dissolved in 3 ml of glacial acetic acid or propionic acid, and 0.1 or 0.2 mole of salicylaldehyde per mole of said L-amino acid salt was added thereto. Then, the free DL-amino acid corresponding to the L-amino acid salt was added to the mixture. Said free DL-amino acid was used in an amount of 0.1 mole per mole of the L-amino acid salt used. The mixture was stirred at 100° C. for one hour if 0.1 mole of salicylaldehyde was used, or for 3 hours if 0.2 mole of salicylaldehyde was used. After the reaction, the degree of the racemization of the L-amino acid salt was estimated in the same manner as described in Experiment 1.

The results are shown in Table 11. It is clear from Table 11 that the racemization of the L-amino acid salt was accelerated by carrying it out in the presence of the free DL-amino acid.

TABLE 11

| Amino acid salt (L-form) | Aliphatic acid | Free amino acid (DL-form)[*1] | Racemization (%) Period of time of reaction | |
|---|---|---|---|---|
| | | | 1 hour | 3 hours |
| Alanine hydrochloride | Acetic acid | (+) | 100 | 100[*2] |
|  |  | (−) | 55 | 77[*2] |
| Alanine benzenesulfonate | Acetic acid | (+) | 88 | 100 |
|  |  | (−) | 13 | 70 |
| Alanine benzenesulfonate | Propionic acid | (+) | 93 | 100 |
|  |  | (−) | 8 | 67 |
| Leucine benzenesulfonate | Acetic acid | (+) | 75 | 100 |
|  |  | (−) | 7 | 54 |
| Methionine hydrochloride | Acetic acid | (+) | 100 | 100[*3] |
|  |  | (−) | 41 | 97[*3] |
| Methionine hydrochloride | Propionic acid | (+) | 96 | 100 |
|  |  | (−) | 69 | 100 |
| Phenylalanine hydrochloride | Acetic acid | (+) | 100 | 100[*2] |
|  |  | (−) | 59 | 100[*2] |
| Phenylalanine hydrochloride | Propionic acid | (+) | 100 | 100 |
|  |  | (−) | 45 | 100 |
| Phenylalanine p-xylene-sulfonate | Acetic acid | (+) | 100 | 100 |
|  |  | (−) | 46 | 100 |

Note:
[*1] (+) means that the racemization reaction was carried out in the presence of the free DL-amino acid, and (−) means that the reaction was carried out in the absence of the free DL-amino acid.
[*2] The racemization reaction was carried out in the presence of 0.05 mole of salicylaldehyde per mole of the L-amino acid salt.
[*3] The racemization reaction was carried out in the presence of 0.1 mole of salicylaldehyde per mole of the L-amino acid salt.

EXPERIMENT 11

0.1 g of L-leucine benzenesulfonate was dissolved in 3 ml of glacial acetic acid, and 0.2 mole of salicylaldehyde per mole of said L-leucine benzenesulfonate was added to the mixture. Further, DL-leucine was added to the mixture. The mixture was stirred at 100° C. for 3 hours. After the reaction, the degree of the racemization of L-leucine benzene-sulfonate was estimated in the same manner as described in Experiment 1.

The results are shown in Table 12. It is clear from Table 12 that the racemization of L-leucine benzenesulfonate was facilitated by carrying it out in the presence of DL-leucine.

Concomitantly, no substantial racemization was observed when L-leucine benzenesulfonate was heated in glacial acetic acid only.

TABLE 12

| Molar ratio of DL-leucine to L-leucine benzenesulfonate | Racemization (%) |
|---|---|
| 0 | 54 |
| 0.001 | 65 |
| 0.01 | 85 |
| 0.05 | 100 |
| 0.1 | 100 |
| 0.2 | 100 |

EXPERIMENT 12

0.1 g of an L-amino acid salt shown in Table 13 was dissolved in 3 ml of glacial acetic acid, and 0.1 mole of an aldehyde shown in Table 13 per mole of said L-amino acid salt was added thereto. Further, the free DL-amino acid corresponding to the L-amino acid salt was added to the mixture. Said free DL-amino acid was used in an amount of 0.1 or 0.2 mole per mole of the L-amino acid salt. Then, the mixture was stirred at 100° C. for one hour. After the reaction, the degree of the racemization of the L-amino acid salt was estimated in the same manner as described in Experiment 1.

The results are shown in Table 13. It is clear from Table 13 that the racemization of the L-amino acid salt was facilitated by carrying it out in the presence of the aldehyde.

TABLE 13

| Aldehyde | Molar ratio of DL-amino acid to the L-amino acid salt | Racemization (%) L-alanine benzene-sulfonate | L-Methionine hydrochloride |
|---|---|---|---|
| — | 0.1 | 0 | 5 |
| Formaldehyde | 0.2 | 46 | 42 |
| Propionaldehyde | 0.2 | 40 | 44 |
| n-Butyraldehyde | 0.1 | 45 | 49 |
| n-Heptylaldehyde | 0.2 | 79 | 73 |
| Acrolein | 0.2 | 48 | 38 |
| Benzaldehyde | 0.1 | 48 | 49 |
| Salicylaldehyde | 0.1 | 88 | 100 |
| p-Hydroxybenzaldehyde | 0.1 | 35 | 44 |
| o-Nitrobenzaldehyde | 0.1 | 39 | 54 |
| 5-Nitrosalicylaldehyde | 0.1 | 76 | 86 |
| Furfural | 0.2 | 91 | 100 |

EXPERIMENT 13

0.1 g of L-methionine hydrochloride was dissolved in 3 ml of glacial acetic acid, and 0.2 mole of DL-methionine per mole of said L-methionine hydrochloride was added thereto. Salicylaldehyde was further added to the mixture. Then, the mixture was stirred at 100° C. for one hour. After the reaction, the degree of the racemization of L-methionine hydrochloride was estimated in the same manner as described in Experiment 1.

The results are shown in Table 14.

TABLE 14

| Molar ratio of salicylaldehyde to L-methionine hydrochloride | Racemization (%) |
|---|---|
| 0 | 9 |
| 0.005 | 53 |
| 0.01 | 71 |
| 0.05 | 100 |
| 0.1 | 100 |
| 0.2 | 100 |

EXPERIMENT 14

0.1 g of an L-amino acid salt shown in Table 15 was dissolved in 3 ml of glacial acetic acid, and salicylaldehyde was added thereto. Said salicylaldehyde was used in an amount of 0.1 mole per mole of the L-amino acid salt. Then, the free DL-amino acid corresponding to the L-amino acid salt was added to the mixture. Said DL-amino acid was used in an amount of 0.2 mole per mole of the L-amino acid salt. The mixture was stirred at 60° C., 80° C. or 100° C. for one hour. After the reaction, the degree of the racemization of the L-amino acid salt was estimated in the same manner as described in Experiment 1.

The results are shown in Table 15. For comparison, the results of the racemization reactions which were carried out without using salicylaldehyde and the free DL-amino acid are also shown in Table 15.

TABLE 15

| Amino acid salt (L-form) | Salicylaldehyde and DL-amino acid*[1] | Racemization (%) 60° C. | 80° C. | 100° C. |
|---|---|---|---|---|
| Alanine benzenesulfonate | (+) | 42 | 86 | 100 |
|  | (−) | 0 | 0 | 0 |
| Methionine hydrochloride | (+) | 49 | 88 | 100 |
|  | (−) | 0 | 0 | 0 |
| Phenylalanine hydrochloride | (+) | 50*[2] | 100*[2] | 100 |
|  | (−) | 0*[2] | 14*[2] | 14*[2] |

Note:
*[1] (+) means that the racemization reaction was carried out in the presence of salicylaldehyde and DL-amino acid, and (−) means that the reaction was carried out in the absence of salicylaldehyde and DL-amino acid.
*[2] The racemization reaction was carried out by suspending L-amino acid salt in glacial acetic acid.

EXAMPLE 1

6 g of a D-amino acid shown in Table 16, 180 ml of glacial acetic acid and 0.2 mole of salicylaldehyde per mole of said D-amino acid were admixed, and the mixture was stirred at 100° C. for one hour. After the reaction, the mixture was condensed under reduced pressure to dryness, and 40 ml of methanol were added to the residue. (In the case of D-lysine, 3.6 ml of conc. hydrochloric acid were further added to the residue.) The crystalline precipitates were collected by filtration. DL-amino acid was thereby obtained as shown in Table 16.

TABLE 16

| D-amino acid | DL-amino acid | | | | |
|---|---|---|---|---|---|
|  | Yield (grams) | (%) | $[\alpha]_D^{25}$ (C = 1, 6N—HCl) | DL-amino acid content (%) | By-product*[2] |
| Alanine | 5.7 | 95.0 | 0 | 100 | Nil |
| Methionine | 5.6 | 93.3 | 0 | 100 | Nil |
| Phenylalanine | 5.6 | 93.3 | 0*[1] | 100 | Nil |

TABLE 16-continued

| D-amino acid | Yield (grams) | (%) | $[\alpha]_D^{25}$ (C = 1, 6N—HCl) | DL-amino acid content (%) | By-product*2 |
|---|---|---|---|---|---|
| Lysine | 6.6 | 90.0 | −1.0 | 95 | Nil |

Note:
*1 $[\alpha]_D^{25}$ (C = 1, H₂O)
*2 The by-product was detected by thin layer chromatography of the product (Solvent; n-butanol:acetic acid:water = 5:1:2).

EXAMPLE 2

10 g of D-proline were dissolved in 60 ml of glacial acetic acid, and 1.8 ml (0.2 mole per mole of said D-proline) of salicylaldehyde were added thereto. The mixture was stirred at 100° C. for one hour. After the reaction, the mixture was condensed, and 70 ml of acetone were added to the residue. The acetone mixture was cooled, and the crystalline precipitates were collected by filtration. 8.8 g of DL-proline were thereby obtained.

Yield: 88%
$[\alpha]_D^{20} + 4.7°$ (C=1, water)
DL-proline content: 94.5%

The product were identified to be pure proline by IR-spectrum and amino acid analysis.

EXAMPLE 3

6 g of L-phenylglycine or L-p-hydroxyphenylglycine were suspended in a mixture of 20 ml of 95% acetic acid and 0.2 ml (0.05 mole per mole of the L-amino acid used) of salicylaldehyde. The suspension was stirred at 100° C. for 2 hours. After the reaction, the mixture was cooled to room temperature, and the crystalline precipitates were collected by filtration and then washed with methanol. DL-phenylglycine or DL-p-hydroxyphenylglycine was thereby obtained. The results are shown in Table 17.

TABLE 17

| L-amino acid | Yield (grams) | (%) | $[\alpha]_D^{25}$ (C = 1, N—HCl) | DL-amino acid content (%) |
|---|---|---|---|---|
| Phenyl-glycine | 5.4 | 90.0 | +1.6° | 99.0 |
| p-Hydroxy-phenyl-glycine | 5.6 | 93.3 | +3.3° | 97.9 |

EXAMPLE 4

3 g of L-serine, 10 ml of 95% acetic acid and 0.04 ml (0.013 mole per mole of L-serine) of salicylaldehyde were admixed. The mixture was stirred at 80° C. for 5 hours. After the reaction, the mixture was cooled to room temperature, and the crystalline precipitates were collected by filtration and then washed with acetic acid. 2.57 g of DL-serine were thereby obtained.

Yield: 85.7%
$[\alpha]_D^{25}$ 0° (C=1, 2N-HCl)
DL-serine content: 100%
The product was chemically pure serine.

EXAMPLE 5

3 g of L-phenylalanine, 90 ml of 80% propionic acid and 0.3 ml (0.2 mole per mole of L-phenylalanine) of n-butyraldehyde were admixed. The mixture was stirred at 100° C. for 3 hours. After the reaction, the mixture was condensed to dryness, and 10 ml of methanol were added to the residue. The methanolic mixture was ice-cooled, and the crystalline precipitates were collected by filtration. 2.70 g of DL-phenylalanine were thereby obtained.

Yield: 90%
$[\alpha]_D^{20} - 1.1°$ (C=1, H₂O)
DL-phenylalanine content: 96.8%
The product was chemically pure phenylalanine.

EXAMPLE 6

6 g of a D-amino acid salt shown in Table 18, 12 ml of glacial acetic acid, 0.1 mole of salicylaldehyde per mole of said D-amino acid salt were admixed. Further, the free DL-amino acid corresponding to the D-amino acid salt was added to the mixture. Said DL-amino acid was used in an amount of 0.1 mole per mole of the D-amino acid salt. The mixture was stirred at 100° C. for 2 hours. After the reaction, the aromatic sulfonic acid corresponding to the D-amino acid salt used was added to the mixture. Said aromatic sulfonic acid was used in an amount of one mole per mole of the free DL-amino acid added. The mixture was condensed under reduced pressure to dryness. 30 ml of acetone were added to the residue, and the crystalline precipitates were collected by filtration. DL-amino acid salt was thereby obtained as shown in Table 18.

TABLE 18

| Amino acid salt (D-form) | Yield (grams) | (%) | $[\alpha]_D^{25}$ (C = 1, H₂O) | DL-amino acid content (%) | By-product* |
|---|---|---|---|---|---|
| Alanine p-toluene-sulfonate | 6.1 | 92.4 | 0 | 100 | Nil |
| Leucine benzene-sulfonate | 5.7 | 86.4 | 0 | 100 | Nil |
| Methionine p-chlorobenzenesulfonate | 6.0 | 90.9 | 0 | 100 | Nil |

Note:
*The by-product was detected by thin layer chromatography of the product (Solvent; n-butanol:acetic acid:water = 5:1:2).

EXAMPLE 7

6 g of D-lysine monohydrochloride were dissolved in 180 ml of an aqueous 95% acetic acid solution, and 0.34 ml of salicylaldehyde was added thereto. The mixture was stirred at 100° C. for 3 hours. After the reaction, the mixture was condensed. 30 ml of 50% ethanol-acetone were added to the residue, and the crystalline precipitates were collected by filtration. 5.6 g of DL-lysine monohydrochloride were thereby obtained.

Yield: 93.3%
$[\alpha]_D^{20} \pm 0°$ (C=1, 6N-HCl)
The product was identified to be chemically pure lysine monohydrochloride by IR-spectrum and thin layer chromatography.

EXAMPLE 8

A mixture of 6 g of L-phenylalanine p-xylenesulfonate, 60 ml of 97% formic acid, 0.85 g of DL-phenylalanine (0.3 mole per mole of L-phenylalanine p-xylenesulfonate) and 0.36 ml of salicylaldehyde (0.2 mole per mole of L-phenylalanine p-xylenesulfonate) were stirred at 100° C. for 4 hours. After the reaction, 1.14 g of p-xylenesulfonic acid dihydrate was dissolved in the mixture, and said mixture was condensed to dryness. 40 ml of acetone were added to the mixture, and said mixture was ice-cooled. The crystalline precipitates were collected by filtration, whereby 6.64 g of DL-phenylalanine p-xylenesulfonate were obtained.

Yield: 85.1%

$[\alpha]_D^{20} -1°$ (C=1, H$_2$O)

Content of DL-form: 90.2%

The product was identified to be chemically pure phenylalanine p-xylenesulfonate by IR-spectrum and thin layer chromatography.

EXAMPLE 9

A mixture of 3 g of D-methionine hydrochloride, 50 ml of propionic acid, 0.48 g of DL-methionine (0.2 mole per mole of D-methionine hydrochloride) and 0.16 ml of benzaldehyde (0.1 mole per mole of D-methionine hydrochloride) was stirred at 100° C. for 2 hours. After the reaction, 0.34 g of 35% hydrochloric acid was added to the mixture, and said mixture was ice-cooled. The crystalline precipitates were collected by filtration, and then washed with acetone. 3.10 g of DL-methionine hydrochloride were thereby obtained.

Yield: 86.1%

$[\alpha]_D^{20} \pm 0°$ (C=1, H$_2$O)

The product was identified to be chemically pure methionine hydrochloride by IR-spectrum and thin layer chromatography.

EXAMPLE 10

A mixture of 0.1 g of L-phenylalanine sulfate, 3 ml of glacial acetic acid, 0.05 mole of salicylaldehyde per mole of L-phenylalanine sulfate was heated at 100° C. in a sealed tube. After the reaction, 10 ml of 1N hydrochloric acid were added to the mixture. Then, the optical rotation of said mixture was examined, and the degree of the racemization was calculated therefrom. As a result, L-phenylalanine sulfate was found to be converted completely into DL-phenylalanine sulfate.

What we claim is:

1. A process for producing a DL-α-amino acid or a salt thereof which comprises racemizing an optically active α-amino acid or a salt thereof at a temperature of 20° to 120° C. in the presence of 2 to 50 g of an aliphatic acid per g of said optically active acid or salt, said aliphatic acid having the formula $$R^1-COOH \quad (I)$$

wherein R$^1$ is hydrogen or alkyl having 1 to 4 carbon atoms, and 0.001 to 0.5 mole of an aldehyde per mole of said optically active acid or salt, said aldehyde having the formula:

$$R^2-CHO \quad (II)$$

wherein R$^2$ is hydrogen; alkyl having 1 to 6 carbon atoms; alkenyl having 2 to 4 carbon atoms; phenyl; phenyl having at least one substituent selected from the class consisting of hydroxy, nitro, amino and alkoxy having 1 to 4 carbon atoms; phenylvinyl; oxygen-containing heteromonocyclic group; and hydroxynaphthyl.

2. The process according to claim 1, wherein the optically active α-amino acid is selected from the group consisting of alanine, valine, leucine, isoleucine, serine, threonine, cystine, cysteine, methionine, tryptophan, phenylalanine, tyrosine, 3-(3,4-dihydroxyphenyl)alanine, phenylglycine, p-hydroxyphenylglycine, arginine, lysine, ornithine, histidine, aspartic acid, glutamic acid, proline and hydroxyproline.

3. The process according to claim 1, wherein the aliphatic acid is a compound of the formula (I) in which R$^1$ is hydrogen or alkyl of one to 3 carbon atoms, and the aldehyde is a compound of the formula (II) in which R$^2$ is hydrogen; alkyl of one to 6 carbon atoms; vinyl; phenyl; phenyl having at least one substituent selected from the class consisting of hydroxy, nitro and methoxy; or furyl.

4. The process according to claim 1, 2 or 3 wherein the aliphatic acid is formic acid, acetic acid or propionic acid, and the aldehyde is formaldehyde, acetoaldehyde, propionaldehyde, n-butyraldehyde, n-heptylaldehyde, acrolein, benzaldehyde, salicylaldehyde, p-hydroxybenzaldehyde, p-anisaldehyde, o-nitrobenzaldehyde, 5-nitrosalicylaldehyde or furfural.

5. The process according to claim 4, wherein the aliphatic acid is acetic acid or propionic acid, and the aldehyde is propionaldehyde, n-butyradehyde, benzaldehyde or salicylaldehyde.

6. The process according to claim 1, 2 or 3, wherein the racemization reaction is carried out at 40° to 100° C.

7. The process according to claim 1, 2 or 3, wherein the racemization reaction is carried out at 60° to 100° C.

8. The process according to claim 1, 2 or 3, wherein 0.005 to 0.2 mole of the aldehyde per mole of the optically active α-amino acid or a salt thereof is used.

9. The process according to claim 1, 2 or 3, wherein 0.01 to 0.2 mole of the aldehyde per mole of the optically active α-amino acid or a salt thereof is used.

10. The process according to claim 1, 2 or 3, wherein the racemization reaction of the optically active α-amino acid salt is carried out in the presence of a free DL-α-amino acid.

11. The process according to claim 10, wherein 0.001 to 0.8 mole of the free DL-α-amino acid per mole of the optically active α-amino acid salt is used.

* * * * *